United States Patent
Sugasawa et al.

(10) Patent No.: US 8,012,971 B2
(45) Date of Patent: Sep. 6, 2011

(54) THERAPEUTIC AGENT FOR CHRONIC OBSTRUCTIVE PULMONARY DISEASE

(75) Inventors: Toshinari Sugasawa, Suita (JP); Takashi Nakajima, Osaka (JP); Hitoshi Fujita, Osaka (JP); Toshio Kanai, Osaka (JP)

(73) Assignee: Dainippon Sumitomo Pharma Co., Ltd., Osaka-Shi, Osaka (JP)

( * ) Notice: Subject to any disclaimer, the term of this patent is extended or adjusted under 35 U.S.C. 154(b) by 561 days.

(21) Appl. No.: 11/919,135

(22) PCT Filed: Apr. 28, 2006

(86) PCT No.: PCT/JP2006/309028
§ 371 (c)(1),
(2), (4) Date: Oct. 24, 2007

(87) PCT Pub. No.: WO2006/118268
PCT Pub. Date: Nov. 9, 2006

(65) Prior Publication Data
US 2009/0131439 A1    May 21, 2009

(30) Foreign Application Priority Data

Apr. 28, 2005 (JP) ................................. 2005-132871
May 26, 2005 (JP) ................................. 2005-154008

(51) Int. Cl.
*A61K 31/426* (2006.01)
*A61K 31/5377* (2006.01)
*C07D 417/10* (2006.01)
*C07D 277/38* (2006.01)

(52) U.S. Cl. ..................... 514/236.8; 514/370; 544/133; 548/194

(58) Field of Classification Search .................. 514/370, 514/377, 236.8; 548/190, 233, 194; 544/133
See application file for complete search history.

(56) References Cited

U.S. PATENT DOCUMENTS

| | | | | |
|---|---|---|---|---|
| 6,919,361 B2 * | 7/2005 | Fujiwara et al. | ............. | 514/371 |
| 7,396,842 B2 * | 7/2008 | Fujiwara et al. | ............. | 514/342 |
| 2004/0072827 A1 | 4/2004 | Fujiwara et al. | | |
| 2005/0222226 A1 | 10/2005 | Fujiwara et al. | | |

FOREIGN PATENT DOCUMENTS

| | | |
|---|---|---|
| EP | 1640369 A1 | 3/2006 |
| JP | 2000-007575 A | 1/2000 |
| JP | 2003192591 A | 7/2003 |
| JP | 2003-321368 A | 11/2003 |
| WO | WO-98/04508 A1 | 2/1998 |
| WO | WO-99/37640 A1 | 7/1999 |
| WO | WO-02/02542 * | 1/2002 |
| WO | WO-02/02542 A1 | 1/2002 |
| WO | WO-03/057693 A1 | 7/2003 |
| WO | WO-03082277 A1 | 10/2003 |

OTHER PUBLICATIONS

Merck Manual pp. 568-582, which correspond to English version Editor, Beers et al., Japanese Version General Superintendent, Sawai, Merck Manual 17th Edition, Japanese Edition, Nikkei Business Publications, Inc., 1999 New, pp. 571 to 585.

Keatings, Vera M., et al., Differences in Interleukin-8 and Tumor Necrosis Factor-α in Induced Sputum from Patients with Chronic Obstructive Pulmonary Disease or Asthma, Am J Respir Crit Care Med, vol. 153, pp. 530-534, 1996.

McDonnell, Neil D., et al. TNF Antagonism, New Drugs for Asthma, Asthma, Allergy and COPD, Prog Respir Res. Basel, Karger, vol. 31, pp. 247-250, 2001.

English version Editor, Beers et al., Japanese version General Superintendent, Sawai, Merck Manual 17th edition, Japanese Edition, Nikkei Business Publications, Inc., 1999 Nen, pp. 571-585.

Nov. 30, 2010 Japanese Final Rejection in corresponding application No. 2007-514847.

* cited by examiner

*Primary Examiner* — Joseph Kosack
(74) *Attorney, Agent, or Firm* — Birch, Stewart, Kolasch & Birch, LLP (57) ABSTRACT

Disclosed is a method for the prevention and/or treatment of a chronic obstructive pulmonary disease by administrating a 5-membered cyclic compound represented by the formula below:

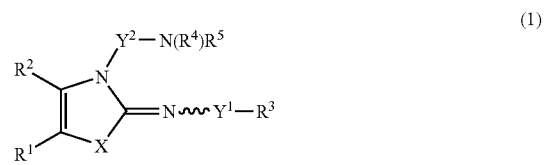

(1)

or a pharmaceutically acceptable salt of the compound or a prodrug of the compound or salt: wherein X represents an oxygen or sulfur atom; $R^1$ represents a hydrogen atom, a substituted or unsubstituted alkyl or the like; $R^2$ represents a hydrogen atom, a substituted or unsubstituted alkyl or the like; $Y^1$ represents single bond, a substituted or unsubstituted alkylene or the like; the wavy line means an (E) or (Z) coordination; $R^3$ represents a hydrogen atom, a substituted or unsubstituted aryl or the like; $Y^2$ represents a substituted or unsubstituted alkylene or an alkenylene; $R^4$ represents a hydrogen atom, a substituted or unsubstituted alkanoyl or the like; and $R^5$ represents a hydrogen atom or a substituted or unsubstituted alkyl.

1 Claim, 2 Drawing Sheets

THERAPEUTIC AGENT FOR CHRONIC OBSTRUCTIVE PULMONARY DISEASE

This application is the National Stage under 35 USC §371 of International Application No. PCT/JP2006/309028 filed Apr. 28, 2006, which claims priority under 35 USC §119(a)-(d) of Application No. 2005-132871 filed in Japan on Apr. 28, 2005, and Application No. 2005-154008 filed in Japan on May 26, 2005.

TECHNICAL FIELD

The present invention relates to a pharmaceutical use of a 5-membered ring compound described in WO 02/02542, or a salt or a pharmaceutical composition thereof. More particularly, the present invention relates to a pharmaceutical use of a 5-membered ring compound, or a salt or a pharmaceutical composition thereof, which is effective for prevention and/or treatment of a chronic obstructive pulmonary disease (COPD).

BACKGROUND ART

It has been reported in Patent Document 1 that a 5-membered ring compound inhibits a late asthmatic response, but no disclosure has been found about an agent for preventing and/or treating COPD which are different from asthma in mechanism of activity and utility.

A chronic obstructive pulmonary disease had been defined as a disease characterized by airflow obstruction (obstructive ventilatory impairment) caused by chronic bronchitis, lung emphysema or a complication thereof, but has been defined as "a disease state characterized by airflow limitation that is not fully reversible. The airflow limitation is usually both progressive and associated with an abnormal inflammatory response of the lungs to noxious particles or gases" in the international guideline GOLD (Global initiative for Chronic Obstructive Lung Disease) published in April, 2001. COPD is also referred to as "a chronic nonspecific lung disease which is manifested an obstructive ventilatory impairment due to lung emphysema or small airway disease caused by harmful gas or particles of cigarette." Cigarette smoking history is important in terms of clinical history. Cigarette smoking is a clear cause of COPD, and an obstructive ventilatory impairment progresses to a chronic progressive disease due to cigarette smoking. Any other causes of COPD include air pollution and occupation (occupation which breathes the fumes, for example a chef), and a promoting factor includes infection. COPD is a progressive irreversible chronic disease, and most part of causes thereof is cigarette smoking. Accordingly, treatment which delays a progression of the disease is smoking cessation, and treatment which significantly contributes to a prognostic improvement after respiratory failure ($PaO_2$ 60 mmHg and below) is a domiciliary oxygen therapy.

It has been reported that neutrophil numbers and concentrations of TNF-α and IL-8 rise by analysis of bronchoalveolar fluid in COPD patients (Non-patent Document 1). Also, it has been suggested by analysis of COPD patients or animal model of disease that an anti TNF-α therapy can be effective for treatment of COPD and inhibition of progression (Non-patent Document 2). Accordingly, an agent effective for treating and/or preventing COPD may be such drugs that inhibit depressed production of IL-8, infiltration/activation of neutrophil, depressed production of TNF-α, infiltration/activation of alveolar macrophage which is one of inflammatory cells which produce IL-8 or TNF-α, thickening of airway epithelium or alveolar wall, or a responsible factor thereof, and further, emphysematous lesion including destruction of alveolar wall or a responsible factor thereof.

Patent Document 1: WO 02/02542
Non-patent Document 1: Am. J. Respir. Crit. Care Med. 153, 530-534 (1996)
Non-patent Document 2: New Drugs for Asthma, Allergy and COPD., Prog. Respir. Res., Basel, Karger, 31, 247-250 (2001)

DISCLOSURE OF INVENTION

Problems to be Resolved by the Invention

The present invention is directed to provide a therapeutic agent useful for improving a chronic obstructive pulmonary disease, comprising a 5-membered ring compound as an active ingredient. Specifically, the present invention is directed to provide a therapeutic agent useful for improving a chronic obstructive pulmonary disease, comprising as an active ingredient N-{2-[2-[(3-fluorophenyl)imino]-4-(4-morpholinophenyl)-thiazol-3(2H)-yl]ethyl}-N'-methylurea. Additionally, the present invention is, in particular, directed to provide a therapeutic agent useful for improving a chronic obstructive pulmonary disease, comprising as an active ingredient N-{2-[2-[(3-fluorophenyl)imino]-4-(4-morpholinophenyl)-thiazol-3(2H)-yl]ethyl}-N'-methylurea, which have been found to have a high therapeutic effect and a high safety without problem of monometabolism.

Means of Solving the Problems

The present inventors have studied to solve the above problems, and found that the present compound inhibits infiltration of an alveolar macrophage, which is one of inflammatory cells which produce TNF-α, and that the problems can be solved according to the following procedures.

More specifically, the present invention is as follows:
(1) A method for preventing and/or treating a chronic obstructive pulmonary disease by administering a 5-membered ring compound of the formula (1):

wherein X is oxygen atom or sulfur atom;
$R^1$ is hydrogen atom, substituted or unsubstituted alkyl, substituted or unsubstituted aryl, or substituted or unsubstituted monocyclic or bicyclic heterocycle;
$R^2$ is hydrogen atom, substituted or unsubstituted alkyl, substituted or unsubstituted aryl, substituted or unsubstituted monocyclic or bicyclic heterocycle, or —$CON(R^6)R^7$;
$R^6$ is hydrogen atom or substituted or unsubstituted alkyl;
$R^7$ is substituted or unsubstituted aryl, substituted or unsubstituted monocyclic heterocycle, or substituted or unsubstituted alkyl; or —$N(R^6)R^7$ may be cyclic imino;
$Y^1$ is single bond, substituted or unsubstituted alkylene, —$CO(CH_2)_n$—, —$SO_2(CH_2)_n$—, —$CONH(CH_2)_n$—, —$CSNH(CH_2)_n$—, or —$COO(CH_2)_n$—;
n is integer of 0 to 5;
wavy line is (E)- or (Z)-coordination;

R³ is hydrogen atom, substituted or unsubstituted aryl, substituted or unsubstituted monocyclic heterocycle, substituted or unsubstituted bicyclic heterocycle, or substituted or unsubstituted cycloalkyl;

Y² is substituted or unsubstituted alkylene, or alkenylene;

R⁴ is hydrogen atom, substituted or unsubstituted alkanoyl, substituted or unsubstituted alkyl, —COOR⁸, —SO₂R⁹, —COR¹⁰, —CON(R¹¹)R¹², —CSN(R¹³)R¹⁴, cycloalkyl, substituted or unsubstituted aryl, substituted or unsubstituted monocyclic heterocycle, —C(=NH)N(R¹⁵)R¹⁶; R⁵ is hydrogen atom, or substituted or unsubstituted alkyl; or —N(R⁴)R⁵ may be cyclic imino;

R⁸ is substituted or unsubstituted alkyl, cycloalkyl, substituted or unsubstituted aryl, or substituted or unsubstituted monocyclic heterocycle; R⁹ is substituted or unsubstituted alkyl, substituted or unsubstituted aryl, or substituted or unsubstituted monocyclic heterocycle; R¹⁰ is cycloalkyl, substituted or unsubstituted aryl, or substituted or unsubstituted monocyclic heterocycle; R¹¹ is hydrogen atom or alkyl; R¹² is hydrogen atom, substituted or unsubstituted alkyl, cycloalkyl, substituted or unsubstituted aryl, substituted or unsubstituted arylcarbonyl, or substituted or unsubstituted monocyclic heterocycle; or —N(R¹¹)R¹² may be cyclic imino; R¹³ is hydrogen atom or alkyl; R¹⁴ is hydrogen atom, substituted or unsubstituted alkyl, cycloalkyl, substituted or unsubstituted aryl, substituted or unsubstituted arylcarbonyl, or substituted or unsubstituted monocyclic heterocycle; or —N(R¹³)R¹⁴ may be cyclic imino;

R¹⁵ is hydrogen atom or alkyl; R¹⁶ is hydrogen atom or substituted or unsubstituted alkyl; or —N(R¹⁵)R¹⁶ may be cyclic imino; or a pharmaceutically acceptable salt or a prodrug thereof.

(2) The method for preventing and/or treating a chronic obstructive pulmonary disease of (1) wherein R¹ is hydrogen atom, X is sulfur atom, Y¹ is single bond, R² is substituted phenyl, —Y²—N(R⁴)R⁵ is —CH₂CH₂—NH(CO)NHCH₃, R³ is meta-substituted phenyl.

(3) The method for preventing and/or treating a chronic obstructive pulmonary disease of (1) wherein the 5-membered ring compound is N-{2-[2-[(3-fluorophenyl)imino]-4-(4-morpholin-4-ylphenyl)-1,3-thiazol-3(2H)-yl]ethyl}-N'-methylurea of the formula (2):

(4) The method for prevention and/or treatment of (3) wherein N-{2-[2-[(3-fluorophenyl)imino]-4-(4-morpholin-4-ylphenyl)-1,3-thiazol-3(2H)-yl]ethyl}-N'-methylurea has a crystal form of needles.

(5) The method for prevention and/or treatment of (3) wherein N-{2-[2-[(3-fluorophenyl)imino]-4-(4-morpholin-4-ylphenyl)-1,3-thiazol-3(2H)-yl]ethyl}-N'-methylurea has a melting point of 190-191° C.

(6) An agent for preventing and/or treating a chronic obstructive pulmonary disease comprising a 5-membered ring compound of the formula (1):

wherein X is oxygen atom or sulfur atom;

R¹ is hydrogen atom, substituted or unsubstituted alkyl, substituted or unsubstituted aryl, or substituted or unsubstituted monocyclic or bicyclic heterocycle;

R² is hydrogen atom, substituted or unsubstituted alkyl, substituted or unsubstituted aryl, substituted or unsubstituted monocyclic or bicyclic heterocycle, or —CON(R⁶)R⁷;

R⁶ is hydrogen atom or substituted or unsubstituted alkyl; R⁷ is substituted or unsubstituted aryl, substituted or unsubstituted monocyclic heterocycle, or substituted or unsubstituted alkyl; or —N(R⁶)R⁷ may be cyclic imino;

Y¹ is single bond, substituted or unsubstituted alkylene, —CO(CH₂)ₙ—, —SO₂(CH₂)ₙ—, —CONH(CH₂)ₙ—, —CSNH(CH₂)ₙ—, or —COO(CH₂)ₙ—;

n is integer of 0 to 5;

wavy line is (E)- or (Z)-coordination;

R³ is hydrogen atom, substituted or unsubstituted aryl, substituted or unsubstituted monocyclic heterocycle, substituted or unsubstituted bicyclic heterocycle, or substituted or unsubstituted cycloalkyl;

Y² is substituted or unsubstituted alkylene, or alkenylene;

R⁴ is hydrogen atom, substituted or unsubstituted alkanoyl, substituted or unsubstituted alkyl, —COOR⁸, —SO₂R⁹, —COR¹⁰, —CON(R¹¹)R¹², —CSN(R¹³)R¹⁴, cycloalkyl, substituted or unsubstituted aryl, substituted or unsubstituted monocyclic heterocycle, —C(=NH)N(R¹⁵)R¹⁶; R⁵ is hydrogen atom, or substituted or unsubstituted alkyl; or —N(R⁴)R⁵ may be cyclic imino;

R⁸ is substituted or unsubstituted alkyl, cycloalkyl, substituted or unsubstituted aryl, or substituted or unsubstituted monocyclic heterocycle; R⁹ is substituted or unsubstituted alkyl, substituted or unsubstituted aryl, or substituted or unsubstituted monocyclic heterocycle; R¹⁰ is cycloalkyl, substituted or unsubstituted aryl, or substituted or unsubstituted monocyclic heterocycle; R¹¹ is hydrogen atom or alkyl; R¹² is hydrogen atom, substituted or unsubstituted alkyl, cycloalkyl, substituted or unsubstituted aryl, substituted or unsubstituted arylcarbonyl, or substituted or unsubstituted monocyclic heterocycle; or —N(R¹¹)R¹² may be cyclic imino; R¹³ is hydrogen atom or alkyl; R¹⁴ is hydrogen atom, substituted or unsubstituted alkyl, cycloalkyl, substituted or unsubstituted aryl, substituted or unsubstituted arylcarbonyl, or substituted or unsubstituted monocyclic heterocycle; or —N(R¹³)R¹⁴ may be cyclic imino;

R¹⁵ is hydrogen atom or alkyl; R¹⁶ is hydrogen atom or substituted or unsubstituted alkyl; or —N(R¹⁵)R¹⁶ may be cyclic imino; or a pharmaceutically acceptable salt or a prodrug thereof.

(7) The agent for preventing and/or treating a chronic obstructive pulmonary disease of (6) wherein R¹ is hydrogen atom, X is sulfur atom, Y¹ is single bond, R² is substituted phenyl, —Y²—N(R⁴)R⁵ is —CH₂CH₂—NH(CO)NHCH₃, R³ is meta-substituted phenyl.

(8) The agent for preventing and/or treating a chronic obstructive pulmonary disease of (6) wherein the 5-membered ring compound is N-{2-[2-[(3-fluorophenyl)imino]-4-(4-morpholin-4-ylphenyl)-1,3-thiazol-3(2H)-yl]ethyl}-N'-methylurea.

(9) The agent for preventing and/or treating a chronic obstructive pulmonary disease of (8) wherein N-{2-[2-[(3-fluorophenyl)imino]-4-(4-morpholin-4-ylphenyl)-1,3-thiazol-3(2H)-yl]ethyl}-N'-methylurea has a crystal form of needles.

(10) The agent for preventing and/or treating a chronic obstructive pulmonary disease of (8) wherein N-{2-[2-[(3-fluorophenyl)imino]-4-(4-morpholin-4-ylphenyl)-1,3-thiazol-3(2H)-yl]ethyl}-N'-methylurea has a melting point of 190-191° C.

(11) A method for preventing and/or treating a chronic obstructive pulmonary disease by administering a 5-membered ring compound of the formula (1):

(1)

wherein X is oxygen atom or sulfur atom;
$R^1$ is hydrogen atom, substituted or unsubstituted alkyl, substituted or unsubstituted aryl, or substituted or unsubstituted monocyclic or bicyclic heterocycle;
$R^2$ is hydrogen atom, substituted or unsubstituted alkyl, substituted or unsubstituted aryl, substituted or unsubstituted monocyclic or bicyclic heterocycle, or —CON($R^6$)$R^7$;
$R^6$ is hydrogen atom or substituted or unsubstituted alkyl; $R^7$ is substituted or unsubstituted aryl, substituted or unsubstituted monocyclic heterocycle, or substituted or unsubstituted alkyl; or —N($R^6$)$R^7$ may be cyclic imino;
$Y^1$ is single bond, substituted or unsubstituted alkylene, —CO(CH$_2$)$_n$—, —SO$_2$(CH$_2$)$_n$—, —CONH(CH$_2$)$_n$—, —CSNH(CH$_2$)$_n$—, or —COO(CH$_2$)$_n$—;
n is integer of 0 to 5;
wavy line is (E)- or (Z)-coordination;
$R^3$ is hydrogen atom, substituted or unsubstituted aryl, substituted or unsubstituted monocyclic heterocycle, substituted or unsubstituted bicyclic heterocycle, or substituted or unsubstituted cycloalkyl;
$Y^2$ is substituted or unsubstituted alkylene, or alkenylene;
$R^4$ is hydrogen atom, substituted or unsubstituted alkanoyl, substituted or unsubstituted alkyl, —COOR$^8$, —SO$_2$R$^9$, —COR$^{10}$, —CON(R$^{11}$)R$^{12}$, —CSN(R$^{13}$)R$^{14}$, cycloalkyl, substituted or unsubstituted aryl, substituted or unsubstituted monocyclic heterocycle, —C(=NH)N(R$^{15}$)R$^{16}$; $R^5$ is hydrogen atom, or substituted or unsubstituted alkyl; or —N($R^4$)$R^5$ may be cyclic imino;
$R^8$ is substituted or unsubstituted alkyl, cycloalkyl, substituted or unsubstituted aryl, or substituted or unsubstituted monocyclic heterocycle; $R^9$ is substituted or unsubstituted alkyl, substituted or unsubstituted aryl, or substituted or unsubstituted monocyclic heterocycle; $R^{10}$ is cycloalkyl, substituted or unsubstituted aryl, or substituted or unsubstituted monocyclic heterocycle; $R^{11}$ is hydrogen atom or alkyl; $R^{12}$ is hydrogen atom, substituted or unsubstituted alkyl, cycloalkyl, substituted or unsubstituted aryl, substituted or unsubstituted arylcarbonyl, or substituted or unsubstituted monocyclic heterocycle; or —N(R$^{11}$)R$^{12}$ may be cyclic imino; $R^{13}$ is hydrogen atom or alkyl; $R^{14}$ is hydrogen atom, substituted or unsubstituted alkyl, cycloalkyl, substituted or unsubstituted aryl, substituted or unsubstituted arylcarbonyl, or substituted or unsubstituted monocyclic heterocycle; or —N(R$^{13}$)R$^{14}$ may be cyclic imino;
$R^{15}$ is hydrogen atom or alkyl; $R^{16}$ is hydrogen atom or substituted or unsubstituted alkyl; or —N(R$^{15}$)R$^{16}$ may be cyclic imino; or a pharmaceutically acceptable salt or a prodrug thereof in combination with a steroid or an anticholinergic agent as a companion drug.

(12) The method for preventing and/or treating a chronic obstructive pulmonary disease of (11) wherein $R^1$ is hydrogen atom, X is sulfur atom, $Y^1$ is single bond, $R^2$ is substituted phenyl, —Y$^2$—N(R$^4$)R$^5$ is —CH$_2$CH$_2$—NH(CO)NHCH$_3$, $R^3$ is meta-substituted phenyl.

(13) The method for preventing and/or treating a chronic obstructive pulmonary disease of (11) wherein the 5-membered ring compound is N-{2-[2-[(3-fluorophenyl)imino]-4-(4-morpholin-4-ylphenyl)-1,3-thiazol-3(2H)-yl]ethyl}-N'-methylurea and the companion drug is a steroid.

(14) The method for preventing and/or treating a chronic obstructive pulmonary disease of (11) wherein the 5-membered ring compound is N-{2-[2-[(3-fluorophenyl)imino]-4-(4-morpholin-4-ylphenyl)-1,3-thiazol-3(2H)-yl]ethyl}-N'-methylurea and the companion drug is an anticholinergic agent.

(15) An agent for preventing and/or treating a chronic obstructive pulmonary disease comprising a 5-membered ring compound of the formula (1):

(1)

wherein X is oxygen atom or sulfur atom;
$R^1$ is hydrogen atom, substituted or unsubstituted alkyl, substituted or unsubstituted aryl, or substituted or unsubstituted monocyclic or bicyclic heterocycle;
$R^2$ is hydrogen atom, substituted or unsubstituted alkyl, substituted or unsubstituted aryl, substituted or unsubstituted monocyclic or bicyclic heterocycle, or —CON($R^6$)$R^7$;
$R^6$ is hydrogen atom or substituted or unsubstituted alkyl; $R^7$ is substituted or unsubstituted aryl, substituted or unsubstituted monocyclic heterocycle, or substituted or unsubstituted alkyl; or —N($R^6$)$R^7$ may be cyclic imino;
$Y^1$ is single bond, substituted or unsubstituted alkylene, —CO(CH$_2$)$_n$—, —SO$_2$(CH$_2$)$_n$—, —CONH(CH$_2$)$_n$—, —CSNH(CH$_2$)$_n$—, or —COO(CH$_2$)$_n$—;
n is integer of 0 to 5;
wavy line is (E)- or (Z)-coordination;
$R^3$ is hydrogen atom, substituted or unsubstituted aryl, substituted or unsubstituted monocyclic heterocycle, substituted or unsubstituted bicyclic heterocycle, or substituted or unsubstituted cycloalkyl;
$Y^2$ is substituted or unsubstituted alkylene, or alkenylene;
$R^4$ is hydrogen atom, substituted or unsubstituted alkanoyl, substituted or unsubstituted alkyl, —COOR$^8$, —SO$_2$R$^9$, —COR$^{10}$, —CON(R$^{11}$)R$^{12}$, —CSN(R$^{13}$)R$^{14}$, cycloalkyl, substituted or unsubstituted aryl, substituted or unsubstituted monocyclic heterocycle, —C(=NH)N(R$^{15}$)R$^{16}$; $R^5$ is hydrogen atom, or substituted or unsubstituted alkyl; or —N($R^4$)$R^5$ may be cyclic imino;

$R^8$ is substituted or unsubstituted alkyl, cycloalkyl, substituted or unsubstituted aryl, or substituted or unsubstituted monocyclic heterocycle; $R^9$ is substituted or unsubstituted alkyl, substituted or unsubstituted aryl, or substituted or unsubstituted monocyclic heterocycle; $R^{10}$ is cycloalkyl, substituted or unsubstituted aryl, or substituted or unsubstituted monocyclic heterocycle; $R^{11}$ is hydrogen atom or alkyl; $R^{12}$ is hydrogen atom, substituted or unsubstituted alkyl, cycloalkyl, substituted or unsubstituted aryl, substituted or unsubstituted arylcarbonyl, or substituted or unsubstituted monocyclic heterocycle; or —N($R^{11}$)$R^{12}$ may be cyclic imino; $R^{13}$ is hydrogen atom or alkyl; $R^{14}$ is hydrogen atom, substituted or unsubstituted alkyl, cycloalkyl, substituted or unsubstituted aryl, substituted or unsubstituted arylcarbonyl, or substituted or unsubstituted monocyclic heterocycle; or —N($R^{13}$)$R^{14}$ may be cyclic imino;

$R^{15}$ is hydrogen atom or alkyl; $R^{16}$ is hydrogen atom or substituted or unsubstituted alkyl; or —N($R^{15}$)$R^{16}$ may be cyclic imino; or a pharmaceutically acceptable salt or a prodrug thereof in combination with a steroid or an anticholinergic agent as a companion drug.

(16) The agent for preventing and/or treating a chronic obstructive pulmonary disease of (15) wherein $R^1$ is hydrogen atom, X is sulfur atom, $Y^1$ is single bond, $R^2$ is substituted phenyl, —$Y^2$—N($R^4$)$R^5$ is —CH$_2$CH$_2$—NH(CO)NHCH$_3$, $R^3$ is meta-substituted phenyl.

(17) The agent for preventing and/or treating a chronic obstructive pulmonary disease of (15) wherein the 5-membered ring compound is N-{2-[2-[(3-fluorophenyl)imino]-4-(4-morpholin-4-ylphenyl)-1,3-thiazol-3(2H)-yl]ethyl}-N'-methylurea and the companion drug is a steroid.

(18) The agent for preventing and/or treating a chronic obstructive pulmonary disease of (15) wherein the 5-membered ring compound is N-{2-[2-[(3-fluorophenyl)imino]-4-(4-morpholin-4-ylphenyl)-1,3-thiazol-3(2H)-yl]ethyl}-N'-methylurea and the companion drug is an anticholinergic agent.

(19) N-{2-[2-[(3-Fluorophenyl)imino]-4-(4-morpholin-4-ylphenyl)-1,3-thiazol-3(2H)-yl]ethyl}-N'-methylurea of the formula (2):

(2)

(20) The compound of (19) which has a crystal form of needles.
(21) The compound of (19) which has a melting point of 190-191° C.

EFFECT OF THE INVENTION

According to the present invention, a chronic obstructive pulmonary disease can be cured.

BEST MODE FOR CARRYING OUT THE INVENTION

Throughout the present specification, each substituent has the following meaning.

The term "alkyl" includes, for example, straight chain or branched chain $C_1$-$C_6$ alkyl, in particular methyl, ethyl, n-propyl, 2-propyl, n-butyl, 2-butyl, 3-methyl-2-propyl, 1,1-dimethylethyl, n-pentyl, n-hexyl or the like.

A substituent of the "substituted alkyl" includes, for example, hydroxy, halogen atom, amino, mono- or di-(alkyl)amino, carboxy, alkoxycarbonyl, alkoxy, carbamoyl, mono- or di-(alkyl)carbamoyl, cyclic imino, alkoxyalkoxy, hydroxyalkoxy, carboxyalkoxy, alkanoyloxy, aryloxy, aryl, arylcarbonylamino, arylamino, arylalkylamino, alkanoylamino, alkylthio, cycloalkyl, arylalkoxy, arylalkyl(alkyl)amino, aryl-sulfonyl, alkylsulfonyl, carbamoylalkoxy, mono- or di-(alkyl)carbamoyl-alkoxy, arylsulfonylamino, arylcarbamoylamino, or the like, wherein the alkyl is optionally substituted by alkoxy, alkoxycarbonyl, carboxy, dialkylamino or hydroxy, and the aryl is optionally substituted by alkyl, alkoxy, halogen atom or hydroxy. The substituent may be selected from the above in single or two or more of the same or different ones. For example, the alkyl may be substituted by 1 to 3, preferably 1 to 2, of the same or different substituent(s) as mentioned above. More preferable substituent of the "substituted alkyl" in $R^4$ includes hydroxy, alkoxy, mono- or di-(alkyl)amino, morpholino, carboxy, alkoxyalkoxy, hydroxyalkoxy, carboxyalkoxy or the like.

The term "alkyl substituted by halogen atom or hydroxy" includes, for example, straight chain or branched chain $C_1$-$C_6$ alkyl substituted by 1 to 3 of halogen atom(s) such as fluorine, chlorine, bromine, iodine or hydroxy, in particular fluoromethyl, difluoromethyl, trifluoromethyl, chloromethyl, bromomethyl, fluoroethyl, 2,2,2-trifluoro-ethyl, 3-fluoro-1-propyl, 3-fluoro-2-propyl, 4-fluoro-1-butyl, 4-fluoro-2-butyl, 3-fluoromethyl-2-propyl, 1,1-di(fluoromethyl)ethyl, 5-fluoro-1-pentyl, 6-fluoro-1-hexyl, hydroxymethyl, 2-hydroxyethyl, 1-hydroxyethyl, 2-hydroxy-1-propyl, 2,3-dihydroxy-1-propyl, 4-hydroxy-1-butyl, 5-hydroxy-1-pentyl, 6-hydroxy-1-hexyl or the like.

The term "alkoxy" includes, for example, straight chain or branched chain $C_1$-$C_6$ alkoxy, in particular methoxy, ethoxy, n-propoxy, 2-propoxy, n-butoxy, 1,1-dimethylethoxy, n-pentyloxy, n-hexyloxy or the like.

A substituent of the "substituted alkoxy" includes, for example, a substituent on the substituted alkyl.

The term "halogen-substituted alkoxy" includes, for example, straight chain or branched chain $C_1$-$C_6$ alkoxy substituted by 1 to 3 of halogen atom(s) such as fluorine, chlorine, bromine or the like, in particular fluoromethoxy, difluoromethoxy, trifluoromethoxy, chloro-methoxy, bromomethoxy, 2-fluoroethoxy, 3-fluoropropoxy, 4-fluoro-butoxy or the like.

The term "alkylamino" includes, for example, amino substituted by straight chain or branched chain $C_1$-$C_6$ alkyl, in particular methyl-amino, ethylamino, n-propylamino, 2-propylamino, n-butylamino, 2-butylamino, 1-methylpropylamino, 1,1-dimethylethylamino, n-pentyl-amino, n-hexylamino or the like.

The term "dialkylamino" includes, for example, amino substituted by two straight chain or branched chain $C_1$-$C_6$ alkyls, in particular dimethylamino, diethylamino, ethylmethylamino, di-n-propyl-amino, di-n-butylamino or the like.

The term "halogen atom" includes, for example, fluorine, chlorine, bromine and iodine, preferably fluorine, chlorine or bromine.

The term "cycloalkyl" includes, for example, $C_3$-$C_8$ cycloalkyl, in particular cyclopropyl, cyclobutyl, cyclopentyl, cyclohexyl, cycloheptyl, cyclooctyl and the like.

A substituent of the "substituted cycloalkyl" includes, for example, alkyl, alkoxy, hydroxy or the like.

The term "cycloalkylalkyl" includes, for example, straight chain or branched chain $C_1$-$C_6$ alkyl substituted by $C_3$-$C_8$ cycloalkyl, in particular cyclopropylmethyl, cyclobutylmethyl, cyclopentylethyl, cyclohexylmethyl, cyclohexylpropyl or the like.

The term "alkoxycarbonyl" includes, for example, straight chain or branched chain $C_1$-$C_6$ alkoxycarbonyl, in particular methoxycarbonyl, ethoxycarbonyl, n-propoxycarbonyl, 2-propoxycarbonyl, n-butoxy-carbonyl, 2-butoxycarbonyl, 1-methylpropoxycarbonyl, 1,1-dimethyl-ethoxycarbonyl, n-pentyloxycarbonyl, n-hexyloxycarbonyl or the like.

The term "alkanoyl" includes, for example, straight chain or branched chain $C_1$-$C_7$ alkanoyl, in particular formyl, acetyl, propanoyl, butanoyl, pentanoyl, pivaloyl, hexanoyl, heptanoyl or the like.

A substituent of the "substituted alkanoyl" includes, for example, the substituent of the substituted alkyl, preferably hydroxy, alkoxy, cyclic imino, carboxy, alkoxyalkoxy, carboxyalkoxy, alkoxycarbonyl, alkanoyloxy, aryloxy, aryl, arylcarbonylamino, arylamino, amino, mono- or di-(alkyl)amino, arylalkylamino, aroylamino, alkanoylamino, alkylthio, halogen atom or the like. More preferable substituent includes hydroxy, alkoxy, dialkylamino, morpholino, carboxy or the like. The substituted alkanoyl may be substituted by 1 to 3, preferably 1 to 2, substituent(s) randomly selected from these groups.

The term "alkylcarbamoyl" includes, for example, straight chain or branched chain $C_1$-$C_6$ alkyl substituted carbamoyl, in particular methylcarbamoyl, ethylcarbamoyl, n-propylcarbamoyl, 2-propyl-carbamoyl, n-butylcarbamoyl, 2-butylcarbamoyl, 3-methyl-2-propyl-carbamoyl, 1,1-dimethylethylcarbamoyl, n-pentylcarbamoyl, n-hexyl-carbamoyl or the like.

The term "dialkylcarbamoyl" includes, for example, carbamoyl substituted by two straight chain or branched chain $C_1$-$C_6$ alkyls, in particular dimethylcarbamoyl, diethylcarbamoyl, ethylmethylcarbamoyl, di-n-propylcarbamoyl, di-n-butylcarbamoyl or the like.

The term "alkylthio" includes, for example, straight chain or branched chain $C_1$-$C_6$ alkylthio, in particular methylthio, ethylthio, n-propylthio, 2-propylthio, n-butylthio, 2-butylthio, 1-methylpropylthio, 1,1-dimethylethylthio, n-pentylthio, n-hexylthio or the like.

The term "alkylsulfinyl" includes, for example, straight chain or branched chain $C_1$-$C_6$ alkylsulfinyl, in particular methylsulfinyl, ethyl-sulfinyl, n-propylsulfinyl, 2-propylsulfinyl, n-butylsulfinyl, 2-butyl-sulfinyl, 1-methylpropylsulfinyl, 1,1-dimethylethylsulfinyl, n-pentyl-sulfinyl, n-hexylsulfinyl or the like.

The term "alkylsulfonyl" includes, for example, straight chain or branched chain $C_1$-$C_6$ alkylsulfonyl, in particular methylsulfonyl, ethylsulfonyl, n-propylsulfonyl, 2-propylsulfonyl, n-butylsulfonyl, 2-butylsulfonyl, 1-methylpropylsulfonyl, 1,1-dimethylethylsulfonyl, n-pentylsulfonyl, n-hexylsulfonyl or the like.

The term "alkylsulfamoyl" includes, for example, straight chain or branched chain $C_1$-$C_6$ alkylsulfamoyl, in particular methylsulfamoyl, ethylsulfamoyl, n-propylsulfamoyl, 2-propylsulfamoyl, n-butylsulfamoyl, 2-butylsulfamoyl, 1-methylpropylsulfamoyl, 1,1-dimethylethylsulfamoyl, n-pentylsulfamoyl, n-hexylsulfamoyl or the like.

The term "dialkylsulfamoyl" includes, for example, sulfamoyl substituted by two straight chain or branched chain $C_1$-$C_6$ alkyls, in particular dimethylsulfamoyl, diethylsulfamoyl, ethylmethylsulfamoyl, di-n-propylsulfamoyl, di-n-butylsulfamoyl or the like.

The term "alkylaminothiocarbonyl" includes, for example, straight chain or branched chain $C_1$-$C_6$ alkyl substituted aminothio-carbonyl, in particular methylaminothiocarbonyl, ethylaminothio-carbonyl, n-propylaminothiocarbonyl, n-butylaminothiocarbonyl, n-pentylaminothiocarbonyl, n-hexylaminothiocarbonyl or the like.

The term "alkylene" includes, for example, straight chain or branched chain $C_1$-$C_6$ alkylene, in particular methylene, ethylene, trimethylene, tetramethylene, pentamethylene, methylethylene, 2-methyltrimethylene, 2,2-dimethyltrimethylene, hexamethylene or the like. A preferable example of the "alkylene" in $Y^2$ includes straight chain or branched chain $C_2$-$C_6$ alkylene, more preferably straight chain or branched chain $C_2$-$C_4$ alkylene, particularly ethylene, trimethylene.

A substituent of the "substituted alkylene" includes, for example, hydroxy, alkoxy, halogen atom, amino, alkanoylamino or the like, and may be substituted by 1 to 3, preferably 1 to 2, substituent(s) randomly selected from these groups. Specific substituted alkylene includes 2-hydroxytrimethylene or the like.

The term "alkenylene" includes, for example, straight chain or branched chain $C_3$-$C_6$ alkenylene, in particular propenylene, butenylene, 2-butenylene, pentenylene, 2-pentenylene, 3-pentenylene or the like.

The term "aryl" includes, for example, $C_6$-$C_{10}$ aryl, in particular phenyl, naphthyl or the like, preferably phenyl.

A substituent of the "substituted aryl" includes, for example, alkyl, alkoxy, halogen-substituted alkoxy, hydroxy, cyclic imino, monocyclic heterocycle, halogen atom, carboxy, cyano, amino, mono- or di-(alkyl)amino, nitro, alkyl substituted by halogen atom or hydroxy, cycloalkyl, cycloalkylalkyl, methylenedioxy, ethylenedioxy, alkoxy-carbonyl, carbamoyl, mono- or di-(alkyl)carbamoyl, alkylthio, alkyl-sulfinyl, alkylsulfonyl, sulfamoyl, alkylsulfamoyl, dialkylsulfamoyl, aryl, aryl substituted by a group selected from alkyl, alkoxy, halogen atom and hydroxy as a substituent or the like. A preferable substituent includes alkyl, alkoxy, halogen-substituted alkoxy, hydroxy, cyclic imino, monocyclic heterocycle, halogen atom, alkyl substituted by halogen atom or hydroxy, methylenedioxy or the like, more preferably alkyl, alkoxy, halogen-substituted alkoxy, hydroxy, cyclic imino, halogen atom, methylenedioxy or the like. A preferable example of a substituent of the "substituted aryl" in $R^1$, $R^2$ and $R^3$ includes alkoxy, di(alkyl)amino, halogen-substituted alkoxy, cyclic imino, halogen atom, alkyl substituted by halogen atom or hydroxy, methylenedioxy or the like, more preferably $C_1$-$C_4$ alkoxy, trifluoromethoxy, morpholino, halogen atom, methylenedioxy or the like. The aryl may be substituted by the same or different 1 to 3, preferably 1 to 2, substituent(s).

The term "aryl substituted by a group selected from alkyl, alkoxy, halogen atom or hydroxy as a substituent" includes, for example, $C_6$-$C_{10}$ aryl (e.g. phenyl, naphthyl) substituted by one or more substituent(s), preferably the same or different 1 to 3, more preferably 1 to 2 substituent(s) selected from a group consisting of straight chain or branched chain $C_1$-$C_6$ alkyl such as methyl, ethyl, n-propyl, 2-propyl, n-butyl, 2-butyl, 1-methylpropyl, 1,1-dimethylethyl, n-pentyl or n-hexyl, straight chain or branched chain $C_1$-$C_6$ alkoxy such as methoxy, ethoxy, propoxy, 2-propoxy, n-butoxy, 1,1-dimethylethoxy, n-pentyloxy or n-hexyloxy, halogen atom such as fluorine, chlorine, bromine or iodine, and hydroxy. In particular, 4-methylphenyl, 2-methylphenyl, 4-(n-propyl)phenyl, 4-(2-propyl)phenyl, 4-(n-butyl)phenyl, 4-methoxyphenyl, 3,4-dimethoxyphenyl, 3,4,5-trimethoxyphenyl, 4-ethoxyphenyl, 4-(n-propoxy)phenyl, 4-(n-butoxy)phenyl, 4-bromophenyl, 4-fluorophenyl, 3,4-difluorophenyl, 4-chlorophenyl, 4-hydroxyphenyl, 2-hydroxyphenyl or the like are included.

The term "cyclic imino" includes, for example, 5- or 6-membered cyclic imino optionally containing additional oxygen atom or nitrogen atom as a ring-forming heteroatom, in particular pyrrolidino, piperidino, morpholino or the like. In cyclic imino for —N($R^6$)$R^7$, a 5- or 6-membered cyclic imino optionally containing additional oxygen atom or nitrogen atom as a ring-forming heteroatom may be optionally fused to benzene ring. An example of such cyclic imino includes, for example, benzopiperidino, benzopyrrolidinyl, benzomorpholino or the like.

The term "monocyclic heterocycle" includes, for example, 5- or 6-membered heterocycle containing 1 to 3 heteroatom(s) selected from nitrogen atom, oxygen atom and sulfur atom, provided that the heterocycle does not contain simultaneously both of oxygen atom and sulfur atom, in particular aromatic heterocycle such as thienyl, furyl, pyrrolyl, pyrazolyl, thiazolyl, isothiazolyl, oxazolyl, isoxazolyl, pyridyl, pyrazinyl, pyrimidinyl or pyridazinyl, or non-aromatic heterocycle such as dioxolanyl, pyranyl or dioxanyl. Preferably, the heterocycle includes aromatic heterocycle, particularly pyridyl.

The term "bicyclic heterocycle" includes, for example, fused heterocycle wherein a 5- or 6-membered heterocycle containing 1 to 3 heteroatom(s) selected from nitrogen atom, oxygen atom and sulfur atom is fused to a benzene ring, provided that the heterocycle does not contain simultaneously both of oxygen atom and sulfur atom, in particular benzofuryl, benzothienyl, indolyl, isoindolyl, indazolyl, quinolyl, isoquinolyl, quinazolyl, phthalazinyl, quinoxalinyl or the like.

A substituent of the "substituted monocyclic heterocycle" and "substituted bicyclic heterocycle" includes, for example, alkyl, alkoxy, halogen atom, hydroxy or the like. The monocyclic heterocycle may be substituted by the same or different 1 to 3, preferably 1 to 2, substituent(s) as mentioned above.

The term "aroyl" includes, for example, $C_7$-$C_{11}$ aroyl, in particular benzoyl, naphthoyl or the like.

The term "prodrug" refers to a compound which is hydrolyzed in vivo to regenerate a 5-membered ring compound of the present invention. The prodrug of the present invention includes any compounds prepared according to any procedures for making a prodrug known to those skilled in the art. For example, in case that a 5-membered ring compound of the present invention has carboxyl group, amino group or the like, a prodrug corresponds to a compound wherein these groups are induced to ester group, amide group or the like which can be easily hydrolyzed in vivo. In case that a 5-membered ring compound has carboxyl group, a prodrug includes a compound wherein the carboxyl group is converted into esters with alkyl (e.g. methyl or ethyl), alkyloxyalkyl (e.g. methyloxymethyl, ethyloxymethyl, 2-methyloxyethyl or 2-methyloxyethyloxymethyl), acyloxymethyl (e.g. pivaloyloxymethyl, acetyloxymethyl, cyclohexylacetyloxymethyl or 1-methylcyclohexylcarbonyloxymethyl), alkoxycarbonylalkyl (e.g. ethyloxy-carbonyloxy-1-ethyl), and cycloalkyloxycarbonylalkyl (e.g. cyclo-hexyloxycarbonyloxy-1-ethyl). In case that a 5-membered ring compound has amino group, a prodrug includes a compound wherein the amino group is converted into acetamide group.

The 5-membered ring compound of the present invention of the formula (1) can be a pharmaceutically acceptable salt thereof. The pharmaceutically acceptable salt includes an acid addition salt and a base addition salt. The acid addition salt includes, for example, an inorganic acid salt such as hydrochloride, hydrobromide, sulfate, and an organic acid salt such as citrate, oxalate, malate, tartrate, fumarate, maleate, and the base addition salt includes an inorganic base salt such as sodium salt, calcium salt, and an organic base salt such as meglumine salt, trishydroxymethylaminomethane salt.

The compound of the present invention may optionally have an asymmetrical center or a substituent having a chiral carbon, and optical isomers may exist. The present invention includes a racemic mixture of these optical isomers and isolated optical isomers. The present invention includes a solvate such as a hydrate of a 5-membered ring compound or a pharmaceutically acceptable salt thereof.

The 5-membered ring compound or a pharmaceutically acceptable salt thereof, or a pharmaceutically acceptable prodrug, and a pharmaceutical composition thereof are useful as an agent for preventing and/or treating a chronic obstructive pulmonary disease.

The 5-membered ring compound has an action in a different mechanism from that of existing agents, and hence it can be used in a combination with any existing agent which has been used for preventing and/or treating the above disease. For example, the compound can be combined with antiallergic agent (e.g. chemical mediator release inhibitor, antihistamine agent, antileukotriene agent, antithromboxane agent or Th2 cytokine inhibitor), steroid drug (e.g. inhaled steroid drug, nasal steroid drug or internal steroid drug), immunosuppressant (e.g. cyclosporine, tacrolimus hydrate or pimecrolimus), xanthine bronchodilator (e.g. theophylline), bronchodilator or nasal dilator (e.g. β stimulant, sympathetic stimulant or parasympatholytic agent such as anticholinergic agent), vaccine therapeutic agent, gold drug, Chinese medicine formulation, a combination of these drugs (e.g. a combination of inhaled β stimulant with inhaled steroid drug), or the like. Especially, when it is used in a combination with steroid drug or a steroid mixture, it enhances the therapeutic effects of the steroid, and thereby it allows to reduce the amount of the steroid drugs or to omit the use of steroid drugs.

The anticholinergic agent includes, for example, tiotropium bromide, ipratropium bromide, flutropium bromide and oxytropium bromide; the antiallergic agent includes, for example, cromoglycic acid, sodium cromoglycate and tranilast; the antihistamine agent includes, for example, diphenhydramine, chlorpheniramine, cetirizine, loratadine, diphenylpyraline, olopatadine, bepotastine, ketotifen, terfenadine, mequitazine, aselastine, epinastine, ozagrel, fexofenadine, ebastine and oxatomide; the antileukotriene agent includes, for example, pranlukast and montelukast; and the Th2 cytokine inhibitor includes, for example, suplatast.

The inhaled β stimulant includes, for example, salmeterol, procatechol, mabuterol, trimetoquinol, tubuterol, theophylline, salbutanol, preferably salmeterol. The steroid drug includes, for example, fluticasone, beclomethasone, prednisolone, dexamethasone, betamethasone, preferably fluticasone. The mixture of the inhaled p stimulant and the inhaled steroid drug includes, for example, a mixture of salmeterol and fluticasone.

The 5-membered ring compound, a pharmaceutically acceptable salt or a pharmaceutically acceptable prodrug thereof and a pharmaceutical composition thereof can be orally or parenterally administered. They can be administered in conventional dosage forms when orally administered. They can be parenterally administered in a dosage form such as topical preparations (e.g. inhalants, nasal preparations and external preparations), injections, transdermal preparations, or transnasal preparations. The oral preparations and rectal preparations include, for example, capsules, tablets, pills, powders, cachets, suppositories and liquid preparations. The injections include, for example, sterile solutions or suspensions. The topical preparations include, for example, creams, ointments, lotions and transdermal preparations such as adhesive preparations.

The above dosage form may be formulated in a conventional manner using a pharmaceutically acceptable excipient or additive. The excipient or additive includes, for example, carrier, binder, flavoring agent, buffering agent, thickening agent, coloring agent, stabilizer, emulsifier, dispersing agent, suspending agent and antiseptic agent. The carrier includes, for example, magnesium carbonate, magnesium stearate, talc, sugar, lactose, pectine, dextrin, starch, gelatin, tragacanth, methylcellulose, sodium carboxymethylcellulose, low melting wax and cocoa butter.

The capsule can be prepared by capsulating a 5-membered ring compound, or a pharmaceutically acceptable salt or a pharmaceutically acceptable prodrug thereof together with a pharmaceutically acceptable carrier combining with or without a pharmaceutically acceptable excipient. The cachet can be also prepared in the similar manner.

The powder may be formulated together with a base for a pharmaceutically acceptable powder. The base includes talc, lactose and starch. A drop can be formulated by combining an aqueous or nonaqueous base with one or more pharmaceutically acceptable diffusing agent, suspending agent, solubilizer or the like.

A liquid preparation for injection includes solution, suspension and emulsion. Such preparation includes, for example, an aqueous solution and aqueous propylene glycol solution. The liquid preparation may optionally contain water. It can be also prepared in the form of a solution of polyethyleneglycol and/or propylene glycol. The liquid preparation suitable for oral administration can be prepared by adding a 5-membered ring compound, or a pharmaceutically acceptable salt or a pharmaceutically acceptable prodrug thereof to water, if necessary, together with coloring agent, flavoring agent, stabilizing agent, sweetening agent, solubilizer or thickening agent. Also, the liquid preparation suitable for oral administration can be prepared by adding a 5-membered ring compound, or a pharmaceutically acceptable salt or a pharmaceutically acceptable prodrug thereof to water with a dispersing agent to improve its viscosity. A thickening agent includes, for example, a pharmaceutically acceptable natural or synthetic rubber, resin, methylcellulose, sodium carboxymethylcellulose or a known suspending agent.

The topical preparation includes the above liquid preparation, cream, aerosol, spray, powder, lotion and ointment. The above topical preparation can be prepared by combining a 5-membered ring compound, or a pharmaceutically acceptable salt or a pharmaceutically acceptable prodrug with a conventional pharmaceutically acceptable diluent and carrier. The ointment and cream may be obtained by adding thickening agent and/or gelling agent to aqueous or oily base to be formulated. The base includes, for example, water, liquid paraffin and vegetable oil. The thickening agent includes, for example, soft paraffin, aluminum stearate, cetostearyl alcohol, propylene glycol, lanolin, hydrogenated lanolin and bees wax. The lotion can be prepared by adding one or more pharmaceutically acceptable stabilizing agent, suspending agent, emulsifier, diffusing agent, thickening agent, coloring agent or flavoring agent to aqueous or oily base. The topical preparation may optionally contain antiseptic agent or antiproliferating agent for bacteria such as methyl hydroxybenzoate, propyl hydroxy-benzoate, chlorocresol or benzalkonium chloride, if necessary. A 5-membered ring compound, or a pharmaceutically acceptable salt or a pharmaceutically acceptable prodrug thereof can be also administered in a dosage form such as liquid preparation spray, powder, dry powder or drop preparation as transpulmonary preparation or inhalant, or transnasal or nasal preparation. Also, liquid preparation or suspension can be used as eye-drops.

A dose or the number of administration of the compound of the present invention depends on conditions, ages, weights, dosage form or the like. In oral administration, the compound of the present invention can be usually administered in the range of about 1 to about 1000 mg, preferably about 2 to about 500 mg, particularly about 5 to about 200 mg per day for adults at one time or by dividing for several times. In injections, the compound of the present invention can be intravenously administered in the range of about 0.1 to about 300 mg, preferably about 1 to about 200 mg at one time or by dividing for several times or continuously. In transpulmonary preparation or inhalant, or transnasal or nasal preparation, the compound of the present invention can be administered in the range of about 0.1 to about 300 mg, preferably about 1 to about 200 mg at one time or by dividing for several times. In external preparation such as ointment or cream, the compound of the present invention can be applied in the range of about 0.1 to about 300 mg, preferably about 1 to about 200 mg at one time or by dividing for several times. In adhesive preparation, the compound of the present invention can be patched in the range of about 0.1 to about 300 mg, preferably about 1 to about 200 mg at one time or by dividing for several times.

Examples by which the present inventors have accomplished the present invention are described in detail below, but the present invention is not intended to be limited to these examples.

(Test Drug)

Theophylline purchased from Sigma-Aldrich was used.

EXAMPLES

Example 1

N-{2-[2-[(3-fluorophenyl)imino]-4-(4-morpholinophenyl)-thiazol-3(2H)-yl]ethyl}-N'-methylurea (SMP-028)

(1) To a solution of acetonitrile (20 ml) containing t-butyl 2-(amino-ethyl)carbamate (1.02 g) was added dropwise 3-fluorophenyl-isothiocyanate (752 mg), and the mixture was heated at 75° C. for 1 hour. The reaction mixture was concentrated in vacuo, crystallized from n-hexane to give t-butyl 2-{[(3-fluoroanilino)carbothioyl]amino}ethyl-carbamate (1.81 g).

¹H-NMR (CDCl₃): δ1.35 (9H, s), 3.35 (2H, m), 3.74 (2H, m), 4.89 (1H, bs), 6.99 (3H, m), 7.37 (1H, m), 7.81 (1H, bs)

(2) A mixture of t-butyl 2-{[(3-fluoroanilino)carbothioyl]amino}ethyl-carbamate (1.81 g) obtained in above (1), α-bromo-4'-morpholino-acetophenone (1.56 g) and ethanol (20 ml) was stirred to heat at 45° C. under nitrogen atmosphere. After 1 hour, the resulting crystal was filtered to give tert-butyl {2-[2-[(3-fluorophenyl)imino]-4-(4-morpholino-phenyl)thiazol-3(2H)-yl]ethyl}carbamate (1.76 g). A mixture of the resulting compound (1.76 g), methanol (5 ml) and a solution of 4N-hydrogen chloride dioxane (50 ml) was stirred at room temperature. After 3 hours, the reaction mixture was concentrated in vacuo, and an insoluble solid was filtered off to give N-[3-(2-aminoethyl)-4-(4-morpholinophenyl)thiazol-2(3H)-ylidene]-3-fluoroaniline (1.57 g). To a mixture of the resulting compound (1.57 g), an aqueous 2N-sodium hydroxide solution (10 ml) and tetrahydrofuran (20 ml) was added phenyl N-methylcarbamate (907 mg), and the mixture was stirred to heat at 55° C. After 3 hours, to a reaction mixture was added water, and the mixture was extracted with ethyl acetate. The organic layer was washed with brine, and then dried over sodium sulfate, and the solvent was removed in vacuo. The residue was crystallized from methanol to give the titled compound (810 mg) as needles.

Figure 1:
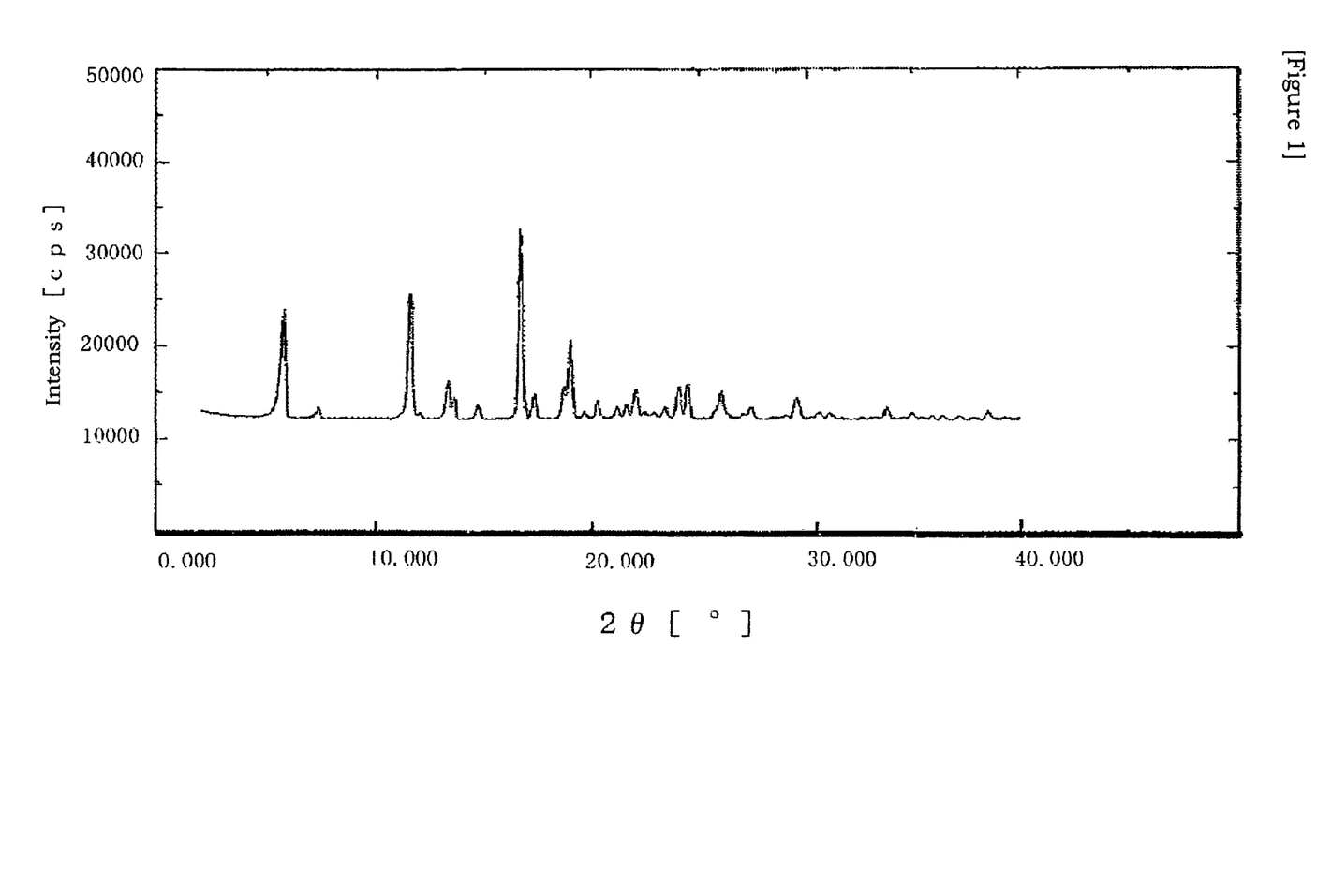
FIG. 1 indicates powder X-ray crystallographic analysis of the compound obtained as needles in Example 1.

Data for 2θ in powder X-ray crystallographic analysis are shown below. Also, a corresponding figure is shown in FIG. 1.

| 2θ | Relative intensity |
|---|---|
| 5.8 | 34 |
| 11.5 | 40 |
| 13.3 | 23 |
| 16.7 | 100 |
| 18.7 | 17 |
| 19.0 | 31 |
| 20.3 | 15 |
| 22.1 | 15 |
| 24.1 | 15 |
| 24.5 | 27 |
| 26.0 | 18 |

Melting point: 190-191° C.
IR: (KBr, cm⁻¹): 3328, 2949, 2852, 1618, 1595, 1577.
¹H-NMR (CDCl₃): δ2.69 (3H, d, J=4.8), 3.26 (4H, t, J=4.8), 3.45 (2H, m), 3.89-3.93 (6H, m), 5.10-5.60 (2H, m), 5.80 (1H, s), 6.80-6.93 (3H, m), 6.97 (2H, d, J=8.8), 7.28-7.54 (3H, m).

Example 2

N-{2-[2-[(3-fluorophenyl)imino]-4-(4-morpholinophenyl)-thiazol-3(2H)-yl]ethyl}-N'-methylurea salt (1) Synthesis of N-{2-[2-[(3-fluorophenyl)imino]-4-(4-morpholin-4-ylphenyl)-1,3-thiazol-3(2H)-yl]ethyl}-N'-methylurea hydrobromide To a suspension of N-{2-[2-[(3-fluorophenyl)imino]-4-(4-morpholin-4-ylphenyl)-1,3-thiazol-3(2H)-yl]ethyl}-N'-methylurea (455 mg) in chloroform (50 ml) was added 25% HBr/AcOH (0.32 g), and the mixture was stirred to dissolve for 30 minutes. The solvent was removed, and then thereto was added diethylether and a precipitate was filtered to give crystals (520 mg) of which a melting point was 191 to 193° C.

(2) Synthesis of N-{2-[2-[(3-fluorophenyl)imino]-4-(4-morpholin-4-yl-phenyl)-1,3-thiazol-3(2H)-yl]ethyl}-N'-methylurea benzenesulfonate Crystals (610 mg) of which a melting point was 153.5 to 156° C. was obtained using benzenesulfonic acid (158 mg) according to the same procedure as mentioned above.

(3) Synthesis of N-{2-[2-[(3-fluorophenyl)imino]-4-(4-morpholin-4-yl-phenyl)-1,3-thiazol-3(2H)-yl]ethyl}-N'-methylurea hydrochloride Crystals (488 mg) of which a melting point was 188 to 189° C. was obtained using a solution (0.25 ml) of 4N hydrochloride dioxane according to the same procedure as mentioned above.

(4) Synthesis of N-{2-[2-[(3-fluorophenyl)imino]-4-(4-morpholin-4-yl-phenyl)-1,3-thiazol-3(2H)-yl]ethyl}-N'-methylurea hydrosulfate

Crystals (530 mg) of which a melting point was 203 to 204° C. was obtained using hydrosulfuric acid (98 mg) according to the same procedure as mentioned above.

(5) Synthesis of N-{2-[2-[(3-fluorophenyl)imino]-4-(4-morpholin-4-yl-phenyl)-1,3-thiazol-3(2H)-yl]ethyl}-N'-methylurea methanesulfonate Crystals (530 mg) of which a melting point was 206 to 207.5° C. was obtained using methanesulfonic acid (96 mg) according to the same procedure as mentioned above.

Example 3

N-{2-[2-[(3-fluoro-4-hydroxyphenyl)imino]-4-(4-morpholinophenyl)-thiazol-3(2H)-yl]ethyl}-N'-methylurea

(1) To a solution of 4-amino-2-fluorophenol in toluene was added phenyl chlorothionoformate, and after 30 minutes thereto was added an aqueous 1N sodium hydroxide solution. The mixture was stirred for 3 hours at room temperature, and then thereto was added t-butyl 2-(aminoethyl) carbamate, and the mixture was stirred overnight to give t-butyl 2-{[(3-fluoro-4-hydroxyanilino)carbothioyl]amino}ethylcarbamate.

(2) The titled compound was obtained using t-butyl 2-{[(3-fluoro-4-hydroxyanilino)carbothioyl]amino}ethylcarbamate obtained in above (1) and α-bromo-4'-morpholinoacetophenone according to the similar procedure to Example 1.

$^1$H-NMR (DMSO-d$_6$): δ2.46 (3H, d, J=4.7), 3.17-3.24 (6H, m), 3.72-3.76 (6H, m), 6.01 (1H, s), 6.63-6.66 (1H, m), 6.75-6.78 (1H, m), 6.87-6.93 (1H, m), 6.99 (2H, d, J=8.85), and 7.29 (2H, d, J=8.85).

Example 4

N-{2-[2-[(3-fluorophenyl)imino]-4-[4-(2-hydroxyethyl)aminophenyl)-thiazol-3(2H)-yl]ethyl}-N'-methylurea Starting from 3-[4-(bromoacetyl)phenyl]-1,3-oxazolin-2-one obtained by reacting 3-(4-acetylphenyl)-1,3-oxazolin-2-one with equal quantity of pyridinium tribromide in chloroform according to the similar procedure to Example 1 gave N-{2-[2-[(3-fluorophenyl)imino]-4-[4-(2-oxo-1,3-oxazolin-3-yl)phenyl]-thiazol-3(2H)-yl]ethyl}-N'-methylurea, and the resulting compound was added to an aqueous solution of 4N sodium hydroxide in methanol, and the mixture was heated to 50° C. After 2 hours, the mixture was standing to cool and the solvent was removed. To a residue was added methanol, and an insoluble was filtered off and methanol was removed. A residue was recrystallized from methanol, 2-propanol to give the titled compound.

$^1$H-NMR (DMSO-d$_6$): δ2.59 (3H, d, J=4.6), 3.24 (2H, q, J=5.9), 3.36 (2H, q, J=6.3), 3.68 (2H, q, J=5.9), 4.84 (2H, t, J=6.4), 4.83 (1H, t, J=5.4), 5.77 (1H, d, J=4.5), 6.04-6.10 (3H, m), 6.74 (2H, d, J=8.6), 6.89-6.98 (3H, m), 7.26 (2H, d, J=8.6), 7.28-54 (1H, m).

Example 5

N-{2-[2-[(3-fluorophenyl)imino]-4-(4-morpholinophenyl)-thiazol-3(2H)-yl]ethyl}-urea N-[3-(2-aminoethyl)-4-(4-morpholinophenyl)thiazol-2(3H)-ylidene]-3-fluoroaniline obtained in Example 1 was dissolved in THF, and thereto was added triethylamine, and then thereto was added 4-nitrophenyl chloroformate under ice-cooling. The mixture was stirred for 2 hours. Thereto was added ammonia water, and the mixture was stirred for 2 hours at room temperature. The resulting compound was recrystallized from methanol to give the titled compound.

$^1$H-NMR (CDCl$_3$): δ3.26 (4H, t, J=4.9), 3.45 (2H, t, J=5.7), 3.89-3.94 (6H, m), 5.79 (1H, s), 6.77-6.90 (3H, m), 6.97 (2H, d, J=8.8), 7.27-7.34 (3H, m).

Example 6

Effects of the Drug on Guinea Pig Chronic Obstructive Pulmonary Disease (COPD) Model (1) A Guinea Pig Chronic Obstructive Pulmonary Disease (COPD) Model An evaluation was carried out as follows according to a report of Kosuke MORIZUMI, Junichi FUCHIGAMI et al., 2002, The 75th Annual Meeting of the Japanese Pharmacological Society (2002) Abstract No. P-259, "Study of a chronic obstructive pulmonary disease-Effects of theophylline on respiratory function and lung function of guinea pigs in an exposure of cigarette smoke."

Male Hartley strain guinea pigs (purchased from Japan SLC, Inc.) were taken in a cigarette exposure holder (RMH-TUBES, manufactured by Muenster Ltd.) to secure them to an exposure chamber (Flow-past type nose-only inhalation chamber, manufactured by Muenster Ltd.), and allowed to inhale cigarette smoke (Hi-Lite, manufactured by Japan Tobacco Inc.) for 60 minutes per day for 5 days in a week, totally 4 weeks using a smoking exposure equipment (Hamburg II, manufactured by Borgwaldt Technik), while the exposure was carried out for 4 days in the 4th week.

(2) Drug Administrations

Each 0.5% MC suspension of a test drug was orally administered daily in 5 ml/weight (kg) once a day for 25 days from the first day of the exposure. To a sham-exposure group and a control group was orally administered a 0.5% MC suspension in a similar manner. Any oral administrations were carried out 0.5 to 1 hours before exposures on a cigarette-smoke-exposure day or after measurements when measuring respiratory functions. A drug was not administered on the day for measurement of respiratory functions after finishing the 4th week of the exposure.

(3) Measurements of Airway Resistance

Specific airway resistances (sRaw) in guinea pigs were measured during awakening by double-flow plethysmography using general respiratory function analysis system (PULMOS-I, manufactured by M•I•P•S Corp.). Measurements were carried out before the exposure and on the day after finishing the 1st, 2nd, 3rd and 4th weeks of the exposure. Each 100 breathings of respiratory functions were individually measured, and the average values were obtained as measured values. A rate of change of airway resistances was calculated by the following equation.

Rate of change of each measured week (%)=100×(a measured value on each measured date−a measured value before starting exposures of cigarette smoke)/a measured value before starting exposures of cigarette smoke Results are shown in Table 1.

Table 1: Effects of the Drug on Airway Resistance (sRaw) Changes in Guinea Pig COPD Model

TABLE 1

| Groups | Dose (mg/kg/day) | Specific airway resistance (sRaw) % increase from pre value | | | |
|---|---|---|---|---|---|
| | | 1 week | 2 weeks | 3 weeks | 4 weeks |
| sham-exposure | — | 4.97$^{NS}$ ± 3.33 | 3.24$^{\#\#}$ ± 6.28 | 10.20$^{\#\#}$ ± 7.19 | 19.41$^{\#}$ ± 5.26 |
| control | 0 | 22.16 ± 8.94 | 52.17 ± 11.23 | 57.02 ± 13.54 | 63.92 ± 13.47 |
| SMP-028 | 10 | 25.54 ± 10.91 | 41.45$^{NS}$ ± 13.12 | 40.60$^{NS}$ ± 12.74 | 51.31$^{NS}$ ± 14.54 |
| SMP-028 | 30 | 15.02 ± 4.07 | 24.29$^{NS}$ ± 8.56 | 34.82$^{NS}$ ± 6.34 | 38.96$^{NS}$ ± 5.17 |
| theophylline | 10 | 15.02 ± 6.73 | 21.66$^{NS}$ ± 9.32 | 22.94$^{NS}$ ± 10.43 | 31.26$^{NS}$ ± 10.60 |

Guinea pigs were exposed to cigarette smoke for 60 min per day, for 5 days per week, for 4 weeks (4 days in last week).
Each value represents mean ± SEM of 8 animals.
$^{\#}$p < 0.05,
$^{\#\#}$p < 0.01 vs. control (Student's t-test or Aspin-Welch test).
$^{NS}$not significant vs. control (Dunnett's test for SMP-028 or Student's t-test for theophylline).

(4) Measurements of Lung Functions

After measuring airway resistances in the 4th week, animals were cut open their tracheas under urethane-anesthetizing (1.6 mg/kg, i.p.), cannulated on the side of lung, fixed by ligation, and measured residual volumes (RV) and functional residual capacities (FRC) by lung functions measuring system (Biosystem for maneuver, manufactured by Buxco Electronics).

Results are shown in Table 2.
Table 2: Effects of the Drug on Changes of Functional Residual Capacity (FRC) and Residual Volume (RV) in Guinea Pig COPD Model

TABLE 2

| Groups | Dose (mg/kg/day) | Functional residual capacity (FRC) (mL) | Residual volume (RV) (mL) |
|---|---|---|---|
| sham-exposure | — | 6.049 ± 0.343 $^{\#\#}$ | 1.906 ± 0.366 $^{\#\#}$ |
| control | 0 | 7.966 ± 0.223 | 3.262 ± 0.188 |
| SMP-028 | 10 | 7.213 ± 0.374 $^{NS}$ | 3.236 ± 0.537 $^{NS}$ |
| SMP-028 | 30 | 7.066 ± 0.353 $^{NS}$ | 2.649 ± 0.649 $^{NS}$ |
| theophylline | 10 | 6.916 ± 0.234 ** | 1.962 ± 0.417 * |

Each value represents mean ± SEM of 8 animals.
$^{\#\#}$ p < 0.01 vs. control (Student's t-test).
* p < 0.05,
** p < 0.01 vs. control (Student's t-test).
$^{NS}$ not significant vs. control (Dunnett's test).

(5) Measurements of Inflammatory Cells in Bronchoalveolar Fluid

After measuring lung functions, animals were exsanguinated to death and opened the thorax, ligated the left bronchial bifurcation, and then injected saline (2.5 mL) into the right lung and aspirated the same via fixed cannula on measuring lung functions repeatedly in twice (totally 5 mL), and the recovery solution was obtained as a bronchoalveolar lavage fluid (BALF). BALF was centrifuged (230×g, 4° C., for 10 minutes) to give cell pellets. The pellets were suspended in saline (0.5 mL), and to a part of the suspension was added Turk solution (manufactured by Wako Pure Chemical Industries, Ltd.) so as to dilute 10 to 20 folds. Leukocyte numbers per 0.1 µL were measured by a blood cell counting chamber and leukocyte numbers per 1 µL were calculated. Cell suspensions were prepared again, smears were prepared using about 2000 to 3000 total cell numbers, May-Grunwald-Giemsa stain was carried out, leukocyte numbers were counted under the microscope, a ratio of each leukocyte number to total leukocyte number was obtained, and each cell number per 1 µL was calculated based on the ratio. Results are shown in each cell number per 1 µL.

The results are shown in Table 3.
Table 3: Effects of the Drug on Changes of Leukocyte Numbers in Bronchoalveolar Fluid in Guinea Pig COPD Model

TABLE 3

| Group | Dose (mg/kg/day) | Cell number in BALF (cells/µL) | | |
|---|---|---|---|---|
| | | Total | Macrophage | Neutrophil |
| sham-exposure | — | 2134 ± 239 $^{\#\#}$ | 1677 ± 196 $^{\#\#}$ | 65 ± 24 $^{\#\#}$ |
| control | 0 | 5484 ± 404 | 3365 ± 259 | 1220 ± 187 |
| SMP-028 | 10 | 4044 ± 419 $^{NS}$ | 2506 ± 313 $^{NS}$ | 1114 ± 193 $^{NS}$ |
| SMP-028 | 30 | 3897 ± 783 $^{NS}$ | 2497 ± 483 $^{NS}$ | 772 ± 277 $^{NS}$ |
| theophylline | 10 | 3578 ± 583 * | 2068 ± 362 * | 1072 ± 322 $^{NS}$ |

Each value represents mean ± SEM of 8 animals.
$^{\#\#}$ p < 0.01 vs. control (Student's t-test or Aspin-Welch test).
* p < 0.05 vs. control (Student's t-test).
$^{NS}$ not significant vs. control
(Dunnett's test for SMP-028 or Student's t-test for theophylline).

(6) Histological Investigations

After collection of BALF, trachea and lung were isolated. The ligation site of the left lung was opened, injected neutral formalin buffer into trachea, bronchi and lung at the pressure of 20 cm $H_2O$ via cannula fixed on the side of the lung, and the lung tissue was extended to be fixed. According to a conventional method, tissue section samples were produced using posterior lobe of the left lung and hematoxylin-eosin (HE) stain was carried out. Any other lung tissues were stored in neutral formalin buffers. Drug efficacies of the produced tissue samples were evaluated by scoring tissue changes under the microscope. The criteria of scores were shown as follows: −: none, ±: minimal, +: mild, ++: moderate, +++: severe. Each quantification was calculated as 0, 1, 2, 3, 4.

Figure 2:
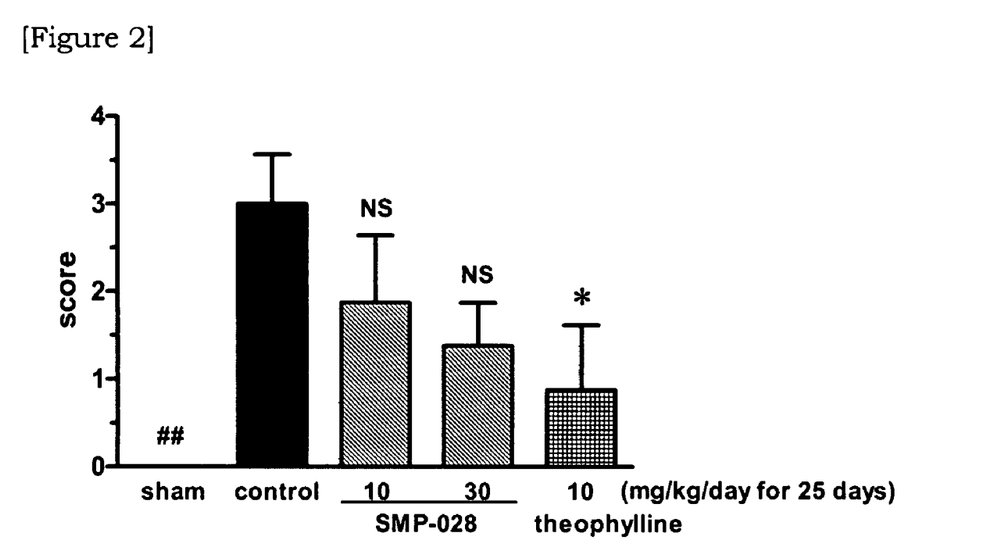
FIG. 2 indicates an effect of the drug on pathological finding changes of lung in guinea pig COPD model in Example 6(6).

Results are shown in Table 4 and FIG. 2.

Table 4: Effects of the Drug on Pathological Finding Changes of Lung in Guinea Pig COPD Model increased by cigarette smoking stimulation relative to those of sham-exposure group. It was shown that the increases of functional residual capacity (FRC) and residual volume (RV) tended to be suppressed in the groups of 10 mg/kg and 30 mg/kg of SMP-028.

As is shown in Table 3, total cell numbers, macrophage and neutrophil in control group were infiltrated into trachea and lung by cigarette smoking stimulation relative to those in sham-exposure group. It was shown that the infiltrations of the inflammatory cells in the airway tended to be suppressed in the groups of 10 mg/kg and 30 mg/kg of SMP-028.

As is shown in Table 4, accumulation of foamy cells/macrophage-like cells within the alveoli and thickening of the alveolar wall by cigarette smoking stimulation were found in control group. Also, minimal hyperplasia of bronchial epithelium, and neutrophil/eosinophil exudate into bronchiolar

TABLE 4

| | Group and dose | | | | | | | | | | | | | | | | |
|---|---|---|---|---|---|---|---|---|---|---|---|---|---|---|---|---|---|
| | sham-exposure | | | | | control | | | | | | SMP-028 10 mg/kg/day for 25 days | | | | | |
| | Number of animals | | | | | | | | | | | | | | | | |
| Findings | 8 | | | | | 8 | | | | | | 8 | | | | | |
| Grade | − | ± | + | ++ | +++ | | − | ± | + | ++ | +++ | − | ± | + | ++ | +++ | |
| A. | 8 | 0 | 0 | 0 | 0 | NS | 7 | 1 | 0 | 0 | 0 | 7 | 1 | 0 | 0 | 0 | |
| B. | 8 | 0 | 0 | 0 | 0 | NS | 7 | 1 | 0 | 0 | 0 | 7 | 1 | 0 | 0 | 0 | |
| C. | 8 | 0 | 0 | 0 | 0 | ## | 1 | 3 | 4 | 0 | 0 | 4 | 2 | 2 | 0 | 0 | NS |
| D. | 8 | 0 | 0 | 0 | 0 | ## | 1 | 3 | 4 | 0 | 0 | 3 | 3 | 2 | 0 | 0 | NS |
| E. | 8 | 0 | 0 | 0 | 0 | NS | 8 | 0 | 0 | 0 | 0 | 8 | 0 | 0 | 0 | 0 | |

| | Group and dose | | | | | | | | | | | |
|---|---|---|---|---|---|---|---|---|---|---|---|---|
| | SMP-028 30 mg/kg/day for 25 days | | | | | | theophylline 10 mg/kg/day for 25 days | | | | | |
| | Number of animals | | | | | | | | | | | |
| Findings | 8 | | | | | | 8 | | | | | |
| Grade | − | ± | + | ++ | +++ | | − | ± | + | ++ | +++ | |
| A. | 8 | 0 | 0 | 0 | 0 | | 7 | 1 | 0 | 0 | 0 | |
| B. | 8 | 0 | 0 | 0 | 0 | | 8 | 0 | 0 | 0 | 0 | |
| C. | 5 | 2 | 1 | 0 | 0 | NS | 7 | 0 | 1 | 0 | 0 | * |
| D. | 3 | 3 | 2 | 0 | 0 | NS | 6 | 1 | 1 | 0 | 0 | * |
| E. | 8 | 0 | 0 | 0 | 0 | | 7 | 1 | 0 | 0 | 0 | |

Findings
A. Hyperplasia, epithelial cell, bronchus
B. Cellular exudation, neutrophil/eosinophil, lumen, bronchiole
C. Thickening, alveolar wall
D. Accumulation, foamy/macrophage-like cell, alveolus
E. Cellular infiltration, neutrophil, alveolus
## p < 0.01 vs. control (Wilcoxon's test).
* p < 0.05 vs. control (Wilcoxon's test).
NS: not significant vs. control (Wilcoxon's test).
NS: not significant vs. control (Steel test)
Grade sign: −: none, ±: minimal, +: mild, ++: moderate, +++: severe.

(7) Evaluation Results

As is shown in Table 1, airway resistances of a control group (exposure group) were raised with time by cigarette smoking stimulation, and significantly increased relative to those of a sham-exposure group (non-exposure group) on the 2nd, 3rd, 4th week of cigarette smoke exposure. It was shown that the increases of airway resistance tended to be suppressed in the groups of 10 mg/kg and 30 mg/kg of SMP-028.

As is shown in Table 2, functional residual capacity (FRC) and residual volume (RV) of control group were significantly lumen were found. These findings are lung lesions similar to human chronic obstructive pulmonary disease. In these pathological changes, it was shown that the accumulation of foamy cells/macrophage-like cells within the alveoli and thickening of the alveolar wall tended to be suppressed in the groups of 10 mg/kg and 30 mg/kg of SMP-028. The results of scoring these pathological findings are shown in FIG. 2. It was shown that the pathological findings tended to be dose-dependently suppressed in SMP-028 relative to those in control group.

It has been found that SMP-028 shows tendency of improving respiratory function, lung function, alveolar destruction and inflammation and prevents progression of these lung lesions caused by smoking stimulation in the present model, and hence, SMP-028 is very useful for a method for treating a chronic obstructive pulmonary disease.

Example 7

Inhibition Tests by Addition of Various CYP Inhibitors

Inhibition tests to various CYP are carried out using test compounds as follows.

Inhibitors and Addition Concentrations

| Furafylline (CYP1A2) | 1 or 10 µM |
|---|---|
| Sulfaphenazole (CYP2C9) | 1 or 10 µM |
| Benzylnilvanol (CYP2C19) | 0.5 or 5 µM |
| Quinidine (CYP2D6) | 0.1 or 1 µM |
| Azamurin (CYP3A4) | 0.5 or 5 µM |
| Montelukast (CYP2C8) | 5 or 50 uM |

Reaction System (Final Concentration)

| Potassium phosphate buffer (Kpi)(pH 7.4) | 50 mM |
|---|---|
| Human liver Ms | 0.5 mg/ml |
| Substrate | 1 µM |
| Inhibitor | 0, 0.1, 1, 5 or 10 µM (See above) |
| NADPH | 1 mM |

Reaction liquid volume 250 µL

Reaction time 15 min n = 2

Additive Amounts Per 1 Tube

| 500 mM | Kpi (pH 7.4) | 25 µl |
|---|---|---|
| 20 mg/ml | human liver Ms | 6.25 µl |
| 5 mM | NADPH | 50 µl |
| 1 mM | substrate | 0.25 µl |
| 0.01, 0.1, 0.5, or 1 mM | inhibitor | 2.5 µl |
| | Purified water | adjust to 250 µl |

Methanol Containing Internal Standard (I.S.)

100 µl of I.S. 10 µg/ml is measured up to 100 ml with methanol.

5 mM NADPH (M.W. 745.43 Purity 82.9%)

NADPH is weighed to dissolve in ion-exchange water.

Experimental Procedure

Mixed solutions of Kpi, Microsome (Ms), substrate and purified water except for NADPH of common components among the above components are prepared.

| For 30 bottles | |
|---|---|
| Kpi | 1000 µl |
| Ms | 250 µl |
| Substrate | 10 µl |
| Purified water | 6640 µl |

Put the mixed solution (197.5 µl) into Eppendorf tube in which inhibitor (2.5 µl) is dispensed.
↓
A reaction is started by adding 5 mM NAPDH (50 µl) to a tube for a 15 min reaction.
↓
Incubation at 37° C. for 15 min.
↓
Quenching by addition of methanol containing I.S. (750 µl).
↓
To a sample in 0 min is added methanol containing I.S. (750 µl), followed by 5 mM NADPH (50 µl).
↓
Suction filtration by a filter plate.
↓
Analyzing by LC-MS/MS (No. 6, API4000).

LC/MS/MS Analysis Condition

| Carrier: 10 mM ammonium acetate buffer (pH 4)/MeOH = A/B Column: Inertsil 2.1*50 mm (3 um), 40° C. Positive | | | |
|---|---|---|---|
| Time (min) | Flow (µl/min) | A % | B % |
| 0.0 | 200 | 95 | 5 |
| 2.0 | 200 | 10 | 90 |
| 5.0 | 200 | 10 | 90 |
| 5.1 | 200 | 95 | 5 |
| 8.0 | 200 | 95 | 5 |

Example 8

Effects of the Drug on Thyroid

C57BL/6 mice (Charles River, male, 6-week old) are received, and after 1 week of quarantine term, normal animals are used in the experiment. Test compounds suspended in 0.5% aqueous methylcellulose solutions (MC) (10 mL/kg) are continuously orally administered once a day for 5 days. Dosages of test compounds are 30, 100 and 300 mg/kg. To a control group is administered 0.5% MC in a similar manner. 9 hours after final administration, mice are treated to collect whole blood from heart under ether-anesthetizing, and serums are separated using Separapid tubes. Separated serums are stored at −80° C. until T4 measurement. T4 is measured by using total thyroxine (T4) enzyme immunoassay test kit (ICN Inc., Cat No. 07B90102).

Example 9

Subacute Toxicity Test

Materials and Method
(1) Test compounds.
(2) Animals: rats, Crj:CD(SD)IGS, male, 5-week old at the start of administration.
(3) A method for preparing administration solutions: Test articles are suspended in 0.5% MC solutions, and dilute solutions are sequentially prepared by using 0.5% MC solutions.

(4) Administration route and method: Gavage administrations are carried out by using disposable syringes and elasticity catheters once a day (in the morning hours).

Observation, Measurement and Assessment;

a. During dosing period
(i) General condition: All animals are observed once or more times a day through the dosing period.
(ii) Weight: All animals are measured on the 1st, 4th, 8th and final date for administration, and further on the day of anatomy.
(iii) Intake: An intake per cage for about continuous 48 hours containing a weight check date is measured once a week through the dosing period.

b. At the end of the dosing period
(i) Hematological assessment
(ii) Blood biochemical assessment
(iii) Organ weights
(iv) Necropsy
(v) Histopathological assessment

INDUSTRIAL APPLICABILITY

The method and the agent of the present invention can be safely applied to a patient with a chronic obstructive pulmonary disease without adverse effects in administration at one time or by dividing for several times per day, and are extremely excellent for preventing and/or treating a chronic obstructive pulmonary disease.

BRIEF DESCRIPTION OF DRAWINGS

FIG. 1.

FIG. 2.

The invention claimed is:

1. A crystalline form of N-{2-[2-[(3-Fluorophenyl)imino]-4-(4-morpholin-4-ylphenyl)-1,3-thiazol-3(2H)-yl]ethyl}-N'-methylurea of the formula (2):

having a needle form showing at least one property selected from:
a) a powder X-ray crystallography having peaks are on 2θ of 5.8, 11.5, 13.3, 16.7, 18,7, 19.0, 20.3, 22.1, 24.1, 24.5, and 26.0; and
b) an infrared absorption spectrum having characteristic absorption bands at 3328, 2949, 2852, 1618, 1595, and 1577 $cm^{-1}$.

* * * * *